United States Patent [19]

Schuh et al.

[11] Patent Number: 4,804,090

[45] Date of Patent: Feb. 14, 1989

[54] SHARPS DISPOSAL SYSTEM

[76] Inventors: Ronald A. Schuh, 3618 N. 97th Pl., Milwaukee; Ralph A. Felton, 8710 N. Kildeer, Brown Deer, both of Wis. 53222

[21] Appl. No.: 90,332

[22] Filed: Aug. 28, 1987

[51] Int. Cl.⁴ .............................................. B65F 1/16
[52] U.S. Cl. .................................. 206/366; 220/1 T; 232/43.1; 206/63.5
[58] Field of Search ............... 220/1 T; 206/366, 63.5; 232/43.1, 43.2, 45, 47

[56]  References Cited

U.S. PATENT DOCUMENTS

| | | | |
|---|---|---|---|
| 1,283,710 | 11/1918 | Evenson | 220/356 |
| 4,315,592 | 2/1982 | Smith | 229/38 |
| 4,410,086 | 10/1983 | Simpson | 206/366 |
| 4,488,643 | 12/1984 | Pepper | 206/366 |
| 4,576,281 | 3/1986 | Kirksey | 206/370 |
| 4,580,688 | 4/1986 | Harris et al. | 220/1 T |
| 4,715,498 | 12/1987 | Hanifl | 220/1 T |
| 4,736,860 | 4/1988 | Bemis | 220/1 T |

Primary Examiner—Joseph Man-Fu Moy
Attorney, Agent, or Firm—Quarles & Brady

[57] ABSTRACT

A disposal system for used and possibly contaminated needles, scalpels and other medical devices, commonly referred to as "sharps", comprises a device for safely transporting the devices and a disposal container. The disposal container is provided with a one-way valve for controlling access to the interior of the container. The one-way valve is preferably a paddle wheel having at least one vane mounted in an opening in a wall of the container. In use the medical device is placed on a vane of the paddle wheel and the paddle wheel rotated to drop the device into the storage container.

12 Claims, 2 Drawing Sheets

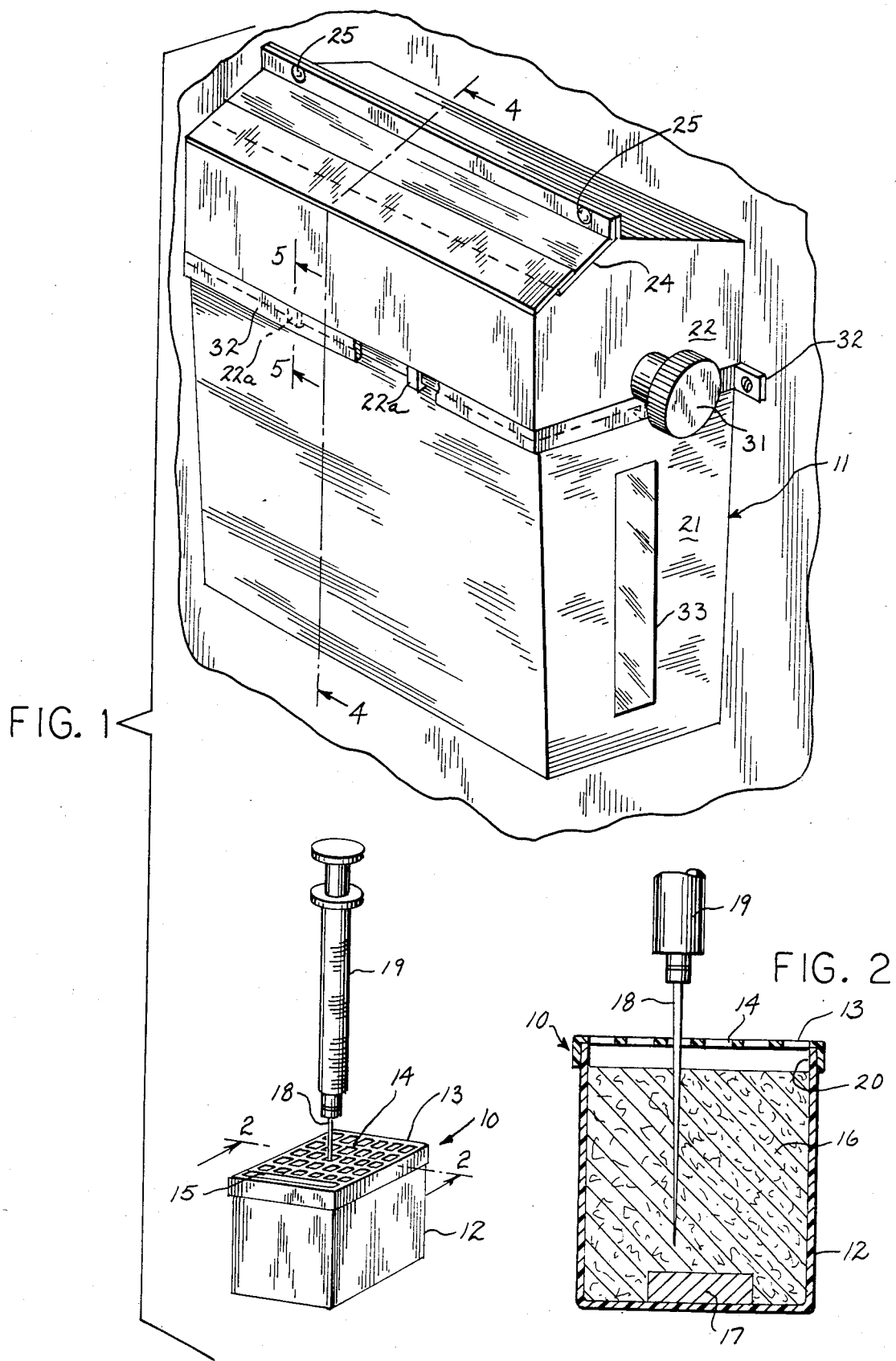

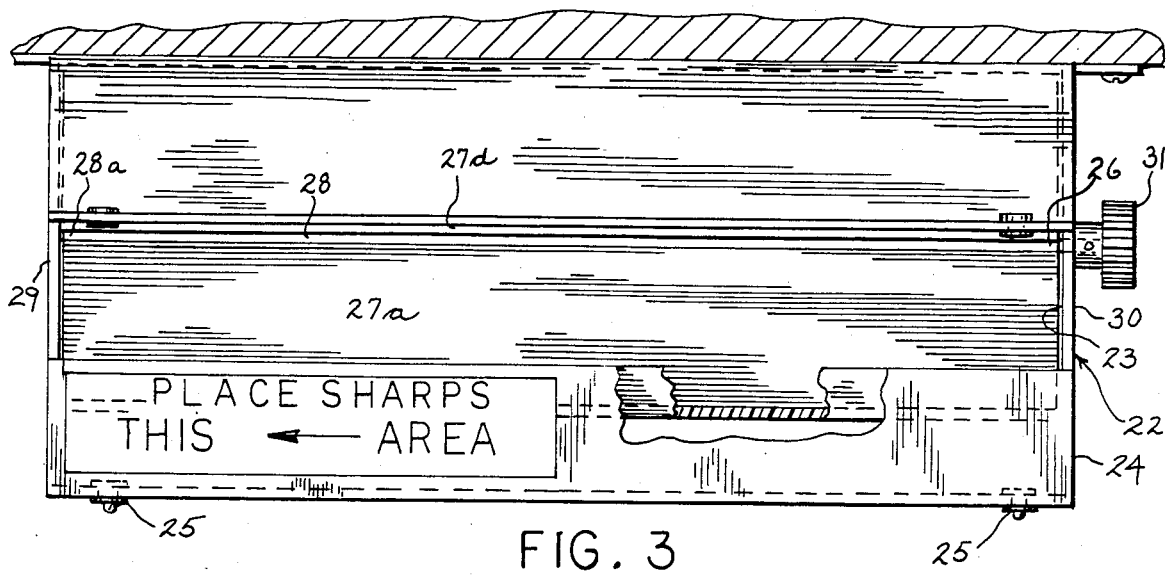
FIG. 3
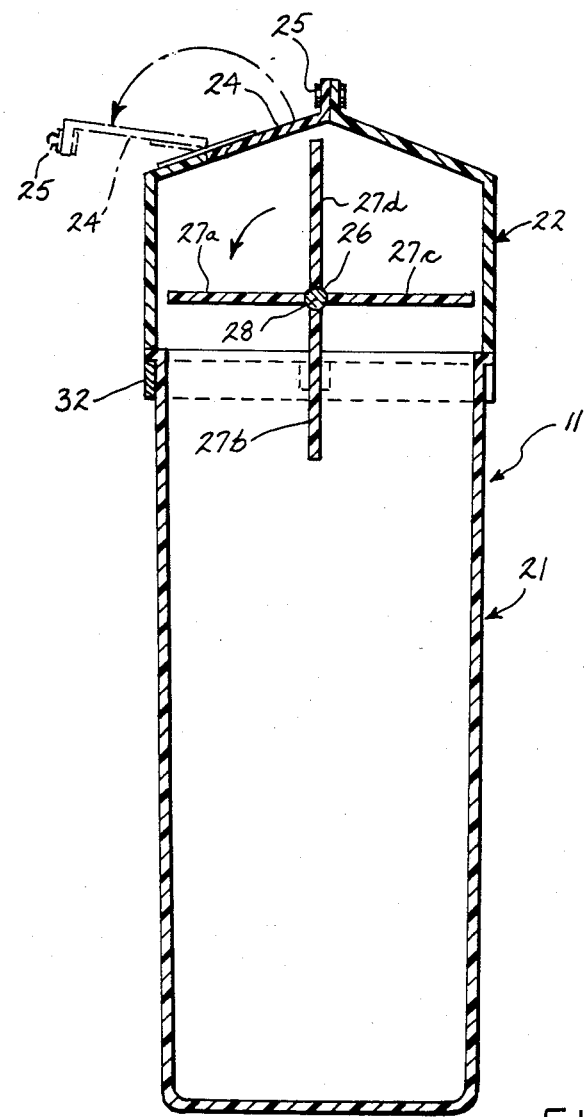
FIG. 4
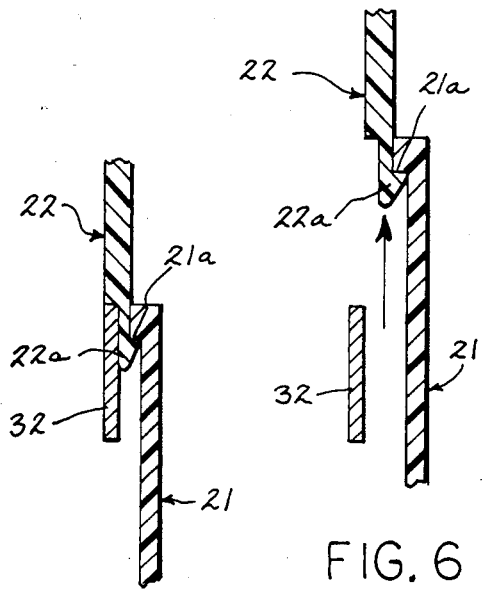
FIG. 5
FIG. 6

SHARPS DISPOSAL SYSTEM

FIELD OF THE INVENTION

The present invention relates generally to medical devices. More particularly, it relates to a disposal system for used needles, scalpels and other sharp medical devices.

BACKGROUND OF THE INVENTION

The utilization of disposable scalpels, syringes and needles, commonly referred to as "sharps," has given rise to problems concerning the safe disposal of these devices. It is frequently discovered that such sharps are the cause of accidental puncture wounds sustained by hospital personnel, or are removed from disposal canisters and fall into the hands of misusers. These sharps may contain a residue of substances which may be harmful, and are frequently contaminated so that contact with the sharps may spread a contagious disease or induce infection. Accidents caused by sharps through skin puncture and disease spreading are frequent causes of injury to medical personnel.

Recently, with the rapid increase in AIDS cases, several regulatory agencies have begun to adopt strict laws regarding disposal and handling of bio-hazardous waste material, including sharps. These laws require the sharps to be seregated from other waste, placed in rigid containers immediately after use and the rigid containers destroyed or buried in a landfill.

Various devices have been proposed for disposal of the sharps. One such device includes a rectangular cardboard container having walls reinforced with several layers of cardboard, an aperture and a flexible aperture cover. A disadvantage associated with this type of disposal device is the lack of an effective closure about the aperture thereby possibly permitting the unwanted, unauthorized removal of the sharps after disposal into the container.

It would be advantageous to have a disposal system that includes a tamper-resistant disposal container with one-way access valve providing ease of insertion of the sharps, while preventing their unauthorized removal. It also would be desirable to have a simple and inexpensive device for transporting sharps from the area of use to the disposal container.

Furthermore, it would be desirable to have a disposal system in which the various components are molded of an inexpensive material which resists puncturing and in which the bulkiest components can be economically stored by stacking.

SUMMARY OF THE INVENTION

The disposal system of the present invention eliminates the disadvantages of prior art devices by providing a simple, inexpensive device for safely transporting sharps and a disposal container with a one-way valve which allows for the easy insertion of the sharps into the disposal container and effectively prevents their subsequent removal.

The device for transporting the sharps to the disposal container is a relatively small cup with a cover having grid-like openings. A solid material in which the sharps can be jammed partially fills the cup and there is a barrier to contaminants between the top of solid material and the bottom of the cover. Sharps are inserted into the solid material through the grid-like openings in the cover.

The disposal container includes a one-way valve which provides access to its interior. The preferred disposal container has a separate lid which interlocks with the remainder of the container so that the components cannot be easily separated.

The components of the disposal system can be made relatively small in overall dimension allowing them to be used in a variety of hospital and office locations.

In a preferred embodiment of the invention, the disposal container includes an aperture which is closed by the one-way valve which is a paddle wheel. The paddle wheel has at least one vane and it is mounted so that it freely rotates or it can be rotated by a handle located on the outside of the disposal container. This construction allows the disposal container to remain effectively closed, preventing tampering and the undesired exposure or removal of its contents.

A unique advantage possessed by the preferred disposal container of the present invention is that the paddle wheel not only serves as a one-way valve but it also provides users with a signal that the disposal container is full and should be replaced. When the disposal container is full, the paddle wheel is prevented from being freely rotated by the vanes encountering discarded items. If desired, the container also can have a transparent wall section to provide a visual gauge of the container contents.

The vanes also help to arrange the sharps in the container more efficiently because each discarded sharp is laid horizontally on a vane and then dropped vertically into the bottom of the storage container. Thus, it is unlikely that the sharps will be stacked haphazardly and inefficiently in the disposal container.

The disposal system of the present invention is a cost effective way of reducing the chance of accidental puncture wounds to medical personnel. Further, the disposal system is of a convenient size which allows it to be located at a patient site, and it is tamper and pilfer resistant. It also resists accidental opening, and thus effectively and safely stores the sharps after insertion.

Numerous other advantages and features of the present invention will become readily apparent from the following description of the invention and from the drawings.

BRIEF DESCRIPTION OF THE DRAWINGS

FIG. 1 is an exploded perspective view of the disposal system of the present invention;

FIG. 2 is an enlarged sectional view taken along lines 2—2 in FIG. 1;

FIG. 3 is an enlarged top view partly in section, of the lid of the disposal container of FIG. 1;

FIG. 4 is an enlarged cross-sectional view taken generally along the plane 4—4 of FIG. 1;

FIG. 5 is an enlarged fragmentary view of the junction of the lid and storage container viewed from plane 5—5 of FIG. 1; and, FIG. 6 is a view similar to FIG. 5.

DESCRIPTION OF THE PREFERRED EMBODIMENT

While the invention is capable of embodiment in several different forms, there is shown in the drawing a preferred embodiment of the invention. It should be understood, however, that the invention is not limited to the embodiment illustrated and that variations may be made by one skilled in the art without departing from the spirit and scope of the invention.

As illustrated in FIG. 1, the disposal system of the present invention comprises a transporting device 10 and a disposal container 11.

As seen in FIG. 1, the transporting device 10 comprises a relatively small, flat bottomed cup 12 with a top cover 13 having grid-like openings 14 and an elongated slot 15. Partially filling the cup 12 is a solid material 16, preferably styrofoam. The cover 13 can be glued or otherwise secured to the cup 12. The transporting device 10 may also contain a stabilizing weight 17 in its bottom (seen only in FIG. 2).

Still referring to FIG. 1, a syringe 19 is seen which has a needle 18 which extends through one of the openings 14 into the solid material 16. With the syringe 19 and needle 18 thus positioned, the combination can be safely transported without fear of accidental contamination or injury. The slot 15 is used in a similar manner to transfer disposable scalpels (not shown) or other contaminated devices that will not fit through an opening 14.

As seen best in FIG. 2, the solid material 16 does not completely fill the cup 12 so that a barrier can be provided to inhibit the movement of contaminants from the solid material 16 to cover 13. In the embodiment of FIG. 2, the barrier is an air space 20 which prevents contaminants in the solid material 16 from contaminating the cover 13. In place of the air space 20 it may be desired to fill the space between the bottom of the cover 13 and top of the material 16 with a solid barrier, such as an absorbent material containing a decontaminant.

In FIGS. 1, 3, 4, 5 and 6, the preferred disposal container 11 is seen in detail.

Referring to FIGS. 1 and 4, it can be seen that the disposal container 11 is comprised of two main components, a receptacle 21 and a lid 22. As seen in FIGS. 1, 4, 5 and 6, the lid 22 and receptacle 21 are provided with coacting flanges 22a and 21a, respectively, that help secure the lid 22 to the receptacle 21. If desired the disposal container 11 could be constructed so that the lid 22 and receptacle 21 are an integral unit which cannot be separated by the user. However, a separate lid 21 and receptacle 22 which can be nested can provide storage and transportation advantages.

Turning now to FIG. 3 it can be seen that the lid 22 has an aperture 23 which is provided with a hinged door 24 which can be secured in a closed position by snap fasteners 25 as seen in FIGS. 1 and 3 or opened to receive sharps as shown in FIG. 3 and in FIG. 4 (dotted lines).

Referring now to FIGS. 3 and 4, it can be seen that a paddle wheel 26 is mounted in the aperture 23 in the lid 22. As seen in FIG. 4, the paddle wheel 26 has four radial vanes 27a, 27b, 27c and 27d which are mounted on an axle 28. The axle 28 is journalled at one end 28a in the side wall 29 of the lid 22 and extends through the other side wall 30 where it operatively engages a knob-like handle 31. The handle 31 is used to rotate the paddle wheel 26. In some embodiments, the handle 31 can be omitted provided the paddle wheel 26 freely rotates when a used medical device is placed on a vane.

The operation of the disposal system of the present invention will now be described. In a hospital room or other location where sharps might be used and disposed of, the disposal container 11 can be placed either on a table or floor or mounted on a wall with a bracket 32 as seen in FIGS. 1 and 5. When any sharps item, such as the hypodermic syringe 19 and needle 18, is desired to be discarded, it is first placed in the transport device 10 as seen in FIGS. 1 and 2 and carried to the disposal container 11. The hinged door 24 of the lid 22 is opened by unsecuring the snap fasteners 25 and the hypodermic syringe 19 and needle 18 combination is removed from the transport container 10 and laid horizontally on the surface of one of the vanes 27a-27d. The combination is positioned with the needle 18 on the area of the vane opposite the legend "Place Sharps in this Area" seen only in FIG. 3. Next the handle 31 is rotated, preferably counterclockwise, whereupon the sharps item falls by gravity from the vane into the receptacle 21.

When the disposal container 11 is no longer needed or it is full as can be ascertained by looking through the transparent wall area 33 or as signaled by the vanes of the paddle wheel 26 encountering resistance from the discarded sharps in the receptacle 21 the hinged door 24 is closed and secured with the fasteners 25. The disposal container 11 is then removed from the bracket 32 by lifting it vertically as seen in FIG. 6. It can then be safely destroyed, preferably by incineration.

The transport device 10 is inexpensive and intended for single patient use. Because of the air space 20 (seen only in FIG. 2) between the top surface of the solid material 16 and the bottom of the cover 13 contamination of the cover by contaminants in the solid material is unlikely. The apertured cover 13 can be cleaned by wiping it with a disinfectant swab (not shown) after each use. The transport device 10 can be destroyed in a similar manner as the disposal container 11.

All the components of the disposal system can be made of a biodegradable material or one that can be incinerated. The preferred material for all components, except the solid material 16, is a tough polypropylene resin which resists penetration by the discarded sharps.

The solid material 16 is preferably a dense polystryene foam which securely retains the sharps after the piercing or cutting parts of the sharps are jammed into it.

The entire disposal system of the present invention can be safely disposed of in accordance with recommended procedures, depending upon its contents. For example, if required, a disposal container with contagious medical waste may have to be autoclaved, if necessary, prior to final disposal.

An improved sharps disposal system has been described which protects health service personnel from puncture wounds and nicks which are the most prevalent hospital accidents. The disposal system of this invention provides for the safe transport and storage and the intact disposal of a wide variety of medical devices.

While this invention has been described in relation to a preferred embodiment, it will be apparent to those skilled in the art that the invention is susceptible to additional embodiments and that certain of the details described herein can be varied considerably without departing from the spirit and scope of the invention. For example, in some instances it may be desired to use a single vane paddle wheel. In addition, in some embodiments the handle can be omitted provided the paddle wheel freely rotates under the weight of the used device when it is placed upon the vane. Therefore, it is intended that the invention not be limited except by the claims.

We claim:

1. A disposal container comprising:

a generally closed hollow container adapted to receive and retain articles;

an access opening formed in said container for receiving articles therein;

means interacting with said container and with said access opening for controlling access to said container through said opening;

said access control means comprising a plurality of members defining articles receiving surfaces adapted to be sequentially positioned to receive articles through said opening and restricting access to the inside of said container.

2. A container as claimed in claim 1 wherein a plurality of said members are exposed to said access opening simultaneously, and wherein said exposed members act to limit access through said opening to the inside of said container.

3. A container as claimed in claim 1 wherein:

said members define a unitary structure in which each of said members are planar members extending substantially radially out from an axis of rotation; and including means supporting said members in said container for rotation about said axis for sequentially positioning successive ones of said members to receive articles through said access opening.

4. A container as claimed in claim 3 wherein said free ends of said members pass closely adjacent to the walls of said container for limiting the size of articles capable of passing therebetween.

5. A container as claimed in claim 1 wherein:

one of said members is positionable to receive an articles inserted into said container through said access opening;

said members being simultaneously movable to effectuate discharge said articles from said one member into said container and simultaneous positioning a next adjacent member to receive articles through said access opening and to preclude access into said container through said access opening.

6. A disposal container for use in disposal of hazardous medical devices comprising:

an open-topped container defining a receptacle for receiving such devices;

a cover member engagable with said open-topped container and substantially permanently attached thereto;

an access opening formed in said cover member for receiving devices to be stored in said container; and access control means disposed internally of said container adjacent to said access opening for controlling passage of articles through said access opening into said container, said access control means comprising a plurality of elongated members defining article receiving surfaces, each of said members being movable in succession to positions for receiving an article inserted through said access opening;

said members being movable as a unit to position successive ones of said members sequentially in said article receiving position, an article discharge position whereby an article thereon is discharged into the container.

7. A container as claimed in claim 6 wherein:

said members are simultaneously positioned in blocking positions to preclude passage of an article through said access opening into said container without movement of said members.

8. A container as claimed in claim 6 wherein said plurality of members are formed into a structure rotatable about an axis of rotation, means supporting said structure for rotation internally of said assembled container and lid;

said members extending generally radially outwardly from said axis of rotation and being unidirectionally rotatable for receiving an article through said access opening and subsequently discharging said article into said container while the next succeeding member is positioned to restrict access into said container and receive an article through said access opening.

9. A container as claimed in claim 8 wherein:

an axle defines the axis of said control means, and said container includes means for receiving said axle in the upper reaches of said container;

said cover means capturing said axle for retaining it in place within the assembled cover and container.

10. A container as claimed in claim 9 wherein said cover member includes a lid for closing said access opening, and means for locking said lid in said closed position.

11. A container as claimed in claim 10 including:

handle means attached to said axle and manually operable for effecting rotation of said members successively past said access opening for receiving articles through said opening and for effective discharge thereof into said container.

12. A sharps container apparatus comprising:

a generally closed hollow container adapted to receive and retain articles;

an access opening formed in said container for receiving articles therein;

means interacting with said container and with said access opening for controlling access to said container through said opening;

said access control means comprising a paddle wheel having at least three vanes with article receiving surfaces, said vanes being adapted to be sequentially positioned to receive articles through said opening, and so arranged that when one vane is in position to receive an article access to the inside of said container is restricted by the others.

* * * * *